(12) United States Patent
Zimmer

(10) Patent No.: US 6,908,900 B2
(45) Date of Patent: Jun. 21, 2005

(54) COMPOSITIONS AND METHODS FOR ENHANCED PHARMACOLOGICAL ACTIVITY THROUGH ORAL AND PARENTERAL ADMINISTRATION OF COMPOSITIONS COMPRISING POLYPEPTIDE DRUG SUBSTANCES AND OTHER POORLY ABSORBED ACTIVE INGREDIENTS

(75) Inventor: Robert H. Zimmer, Mulhouse (FR)

(73) Assignee: Zimmer & Associates AG, Reinach (CH)

( * ) Notice: Subject to any disclaimer, the term of this patent is extended or adjusted under 35 U.S.C. 154(b) by 34 days.

(21) Appl. No.: 10/050,903

(22) Filed: Jan. 16, 2002

(65) Prior Publication Data

US 2002/0132777 A1 Sep. 19, 2002

Related U.S. Application Data

(60) Provisional application No. 60/262,337, filed on Jan. 17, 2001, provisional application No. 60/332,636, filed on Nov. 6, 2001, provisional application No. 60/287,872, filed on May 1, 2001, and provisional application No. 60/287,886, filed on May 1, 2001.

(51) Int. Cl.$^7$ .................................................. C07K 7/00
(52) U.S. Cl. ............................ 514/17; 514/2; 530/300; 530/350
(58) Field of Search ........................ 514/17, 2; 530/326

(56) References Cited

U.S. PATENT DOCUMENTS

| | | |
|---|---|---|
| 4,239,754 A | 12/1980 | Sache et al. |
| 4,339,534 A | 7/1982 | Johansen et al. |
| 4,396,606 A | 8/1983 | Goldstein |
| 4,694,006 A | 9/1987 | Bundgaard et al. |
| 4,925,673 A | 5/1990 | Steiner et al. |
| 5,212,158 A | 5/1993 | Vandai |
| 6,136,952 A * | 10/2000 | Li et al. ................. 530/326 |
| 2002/0090603 A1 * | 7/2002 | Lipton et al. .............. 435/4 |

FOREIGN PATENT DOCUMENTS

WO  WO 98/11126  3/1998

OTHER PUBLICATIONS

Fukushima, K., Hypoglycemic Effect and Enhanced Gastrointestinal Absorption of Insulin Using New Cinnamoyl–phenylalanine Derivatives, Hokkaido Journal of Medical Science, vol. 71, No. 6, 1996, pp. 727–743.

Vergnolle, N, et al., Proteinase–Activated Receptor 2 (PAR$_2$)–Activating Peptides: Identification of a Receptor Distinct From PAR$_2$ That Regulates Intestinal, Transport, Proceedings of the National Academy of Sciences of USA, National Academy of Science, vol. 95, (Jun. 1998), pp. 7766–7771.

Langguth, P., et al., The Challenge of Proteolytic Enzymes in Intestinal Peptide Delivery, Journal of Controlled Release, Elsevier Science Publishers B.V. Amsterdam, NL, vol. 46, No. 1, May 1997, pp. 39–57.

Egleton, R. D., et al., Improved Bioavailability to the Brain of Glycosylated Met–Enkephalin Analogs, Brain Research, vol. 881, No. 1, 2000, pp. 37–46.

Pauletti, G. M., et al., Improvement of Oral Peptide Bioavailability: Peptidomimetics and Prodrug Strategies, Advanced Drug Delivery Review, vol. 27, No. 2–3, 1997, pp. 235–256.

Ahlers, et al., Enhanced Immunogenicity of HIV–1 Vaccine Construct By Modification of the Native Peptide Sequence, Proc. Natl. Acad. Sci. USA, vol. 94, pp. 10856–10861, Sep. 1997.

Greenstein, et al., A Universal T Cell Epitope–Containing Peptide From Hepatitis B Surface Antigen Can Enhance Antibody Specific For HIV gp120, Journal of Immunology, vol. 148, pp. 3970–3977, No. 12, Jun. 1992.

Belyakov, et al., The Importance of Local Mucosal HIV–Specific CD8* Cytotoxic T Lymphocytes For Resistance to Mucosal Viral Transmission in Mice and Enhancement of Resistance by Local Administration of IL–12, The Journal of Clinical Investigation, vol. 102(12); pp. 2072–2081, Dec. 1998.

Belyakov, et al., Mucosal Immunization With HIV–1 Peptide Vaccine Induces Mucosal and Systemic Cytotoxic T Lymphocytes and Protective Immunity in Mice Against Intrarectal Recombinant HIV_Vaccinia Challenge, Proc. Natl. Acad. Sci. USA, vol. 95, pp. 1709–1714, Feb. 1998.

Patel, et al., Oral Administration of Insulin By Encapsulation Within Liposomes, North–Holland Publishing Company, vol. 62, No. 1, pp. 60–63, Feb. 1976.

Hashimoto, et al., ACTH Release in Pituitary Cell Cultures, Effect of Neurogenic Peptides and Neurotransmitter Substances Corticotropin Releasing Factor (CRF), Endocrinol. Japan, vol. 26 (1), pp. 103–109, Feb. 1979.

* cited by examiner

Primary Examiner—Christopher Tate
Assistant Examiner—Roy Teller
(74) Attorney, Agent, or Firm—McCarter & English, LLP

(57) ABSTRACT

Disclosed herein are novel pharmaceutical agents and compositions, as well as novel methods, to enhance the absorption of polypeptide drug substances that normally display little if any absorbability if administered orally. Also disclosed are novel compositions and methods to significantly enhance the bioavailability and pharmacological efficacy of polypeptide drug substances whether administered orally or parenterally.

14 Claims, No Drawings

COMPOSITIONS AND METHODS FOR ENHANCED PHARMACOLOGICAL ACTIVITY THROUGH ORAL AND PARENTERAL ADMINISTRATION OF COMPOSITIONS COMPRISING POLYPEPTIDE DRUG SUBSTANCES AND OTHER POORLY ABSORBED ACTIVE INGREDIENTS

REFERENCE TO RELATED APPLICATIONS

This application claims benefit under Title 35, U.S.C. § 119(e), of U.S. Applications Ser. Nos. 60/262,337, filed 17 Jan. 2001; 60/332,636, filed 6 Nov. 2001; 60/287,872, filed 1 May 2001; and 60/287,886, also filed 1 May 2001.

FIELD OF THE INVENTION

This invention, in general, relates to compositions and methods that permit oral and parenteral administration, and significantly enhance the bioavailability and pharmacological effects of therapeutically active polypeptides, pseudo-peptides and peptide mimics, particularly those that are otherwise poorly orally absorbable or display only minimal bioavailability if administered parenterally.

BACKGROUND OF THE INVENTION

It has been observed in the literature that therapeutically effective polypeptides ($aa_n$) with two or more amino acids ($n \geq 2$) are poorly absorbed orally. Even a polypeptide of as few as two amino acids, or related structures, exhibits very narrow absorption windows and poor bioavailability. As an example, the Physician's Desk Reference (PDR) reports that the angiotensin converting enzyme (ACE) inhibitor Enalaprilat ($R_1$-Ala-Pro; n=2) is very poorly absorbed orally. Enalapril ($R_2$-Ala-Pro), which is a pro-drug of Enalaprilat, is better absorbed orally, but the end result demonstrates only a 25% relative bioavailability of the active moiety (Enalaprilat) released from in vivo cleavage of the prodrug. In comparison, Lisinopril ($R_3$-Lys-Pro) has relatively good solubility in water, but only a moderate oral bioavailability (<25%), with a $T_{max}$ (time to maximum serum levels in vivo) of more than seven hours. Thus, this class of therapeutic species is preferably administered via a non-oral deliver method, such as by injection. However, even delivered intravenously, the therapeutically active species has a relatively short serum half-life.

It is also known that some tri-peptides originating in food products may be capable of effective oral absorption, but to an unknown extent. Furthermore, no active tri- or longer peptide drug substances ($n \geq 3$) displaying oral absorption have been identified.

In a currently pending U.S. patent application Ser. No. 09/844,426, the disclosure of which is hereby incorporated by reference in its entirety, the present inventors disclosed a method permitting the oral absorption of polypeptide drug substances ($aa_n$) and other poorly orally absorbed drugs. We have subsequently made the surprising discovering that additional carrier systems can be effective to achieve similar enhancement of pharmacological activity for poorly absorbed active drug species, and that an optional, more sophisticated linker offers additional improvement in results. Furthermore, we have discovered that, through practice of the methods of the present invention, the length of the polypeptide drug entity (n) can be increased, particularly when the composition is administered parenterally, such as by intravenous (i.v.) administration, with the result of drastically improved pharmacological and therapeutic effects for the active drug moiety. Accordingly, through the practice of the present invention, it is possible to chemically modify a polypeptide species (or, additionally, pseudo-peptides or peptide mimics) of known therapeutic utility to both permit the oral administration of the species and to drastically improve its pharmacological properties even when administered through a parenteral route.

In the present disclosure, the word "peptide" corresponds to any sequence of naturally occurring amino acids, as well as to pseudo-peptides and to peptide mimics. By "pseudo-peptide," we mean a chemical modification of one or more of the amino acid residues constituting the peptide or of their bonds such as, but not limited to, use of amino acids in their D-configuration, use of N-methyl amino acids, replacement of one or more peptidic bonds (—CO—NH) by a reduced bond (—$CH_2NH$) and/or by —NHCO, —$CH_2CH_2$, —$COCH_2$, —$CHOHCH_2$, —CH2O. By "peptide mimic," we mean any amino acid sequence in which the —C-backbone has been replaced by an oligourea backbone or an oligocarbamate backbone. We also include ω-peptides in this definition.

SUMMARY OF THE INVENTION

In a first embodiment, the present invention provides a pharmaceutical agent comprising a carrier moiety and a therapeutically active peptide species, wherein the peptide is in the form $aa_n$, where n is the number of amino acid residues in the peptide. Preferably, the carrier moiety comprises an aryl or alkyl group of sufficient length or steric bulk to protect the active peptide species from enzymatic degradation in vivo. More preferably, the carrier is selected from a group comprising cinnamoyl, benzoyl, phenylacetyl, 3,4-methylenedioxycinnamoyl, 3,4.5-trimethoxycinnamoyl t-butoxycarbonyl, benzyloxycarbonyl, pivaloyl, N-9-fluorenylmethoxycarbonyl, and fumaroyl. Furthermore the carrier moiety can be chemically linked to a therapeutically active peptide species of the general formula $aa_n$, where n is an integer from 2 to 40. In addition, this embodiment of the present invention contemplates a therapeutically active peptide species that is poorly absorbed orally. Preferably, n is an integer from 3 to 6. More preferably, n is 5. More preferably still, the therapeutically active peptide species comprises Tyr-Gly-Gly-Phe-Met (SEQ ID NO: 1).

In an alternative embodiment, the pharmaceutical agent of the present invention further comprises a linker species linking the peptide to the carrier moiety. Preferably, the linker species is selected from the group consisting of a natural peptide, a pseudo-peptide, and a peptide mimic, each member of the group comprising 4 or fewer amino acid residues. In one aspect of this embodiment of the present invention, the linker species is directly bound to the carrier. Alternatively, the linker species is bound to the carrier through a —$C_6$ or —$C_8$ acidic moiety. More preferably, the linker species is Gly-carba-Gly, a pseudo-peptide. More preferably still, the linker species is associated with a —$C_n$ chain, where n is an integer from 6 to 8.

In another embodiment, the present invention provides a pharmaceutical composition for administration to a patient in need thereof comprising the pharmaceutical agent described immediately above, and one or more pharmaceutically acceptable adjuvants. Preferably, the composition is formulated for oral administration. Alternatively, the composition is formulated for parenteral administration. Preferably, the composition is formulated for intravenous administration. This embodiment of the present invention also contemplates a composition that releases a biologically active form of the pharmaceutical agent into the patient's system at physiologically effective levels over a period of time of up to twelve hours. Preferably, the composition releases a biologically active form of the pharmaceutical agent into the patient's system at physiologically effective levels over a period of time of up to twenty-four hours. In this embodiment of the present invention, the peptide species is preferably an epitope or an immune sequence characteristic of an infectious, viral or cancerous disease.

In yet another embodiment, the present invention contemplates a method for the treatment of a physiological condition through administration of a therapeutically effective species comprising the steps of chemically linking a therapeutic polypeptide of the general formula $aa_n$, where aa is an amino acid, and where n is an integer from 2 to 40, to an alkyl or aryl carrier moiety to form a pro-drug, and administering the pro-drug to a patient exhibiting the physiological condition. Preferably, the therapeutic polypeptide used in the practice of the invention is poorly absorbed orally, and the carrier moiety is selected from the group comprising cinnamoyl, benzoyl, phenylacetyl, 3,4-methylenedioxycinnamoyl, 3,4,5-trimethoxycinnamoyl, t-butoxycarbonyl, benzyloxycarbonyl, pivaloyl, N-9-fluorenylmethoxycarbonyl, and fumaroyl Alternatively, this embodiment of the present invention provides a method wherein the pro-drug is administered orally or parenterally. In yet another alternative of the present embodiment, the method contemplates the use of a therapeutic polypeptide that is chemically linked to the carrier moiety through a linker species.

In still another alternative embodiment, the present invention provides a method to enhance the absorption and bioavailability of an active polypeptide drug substance of the form $aa_n$ in a pharmaceutical formulation, the method comprising the steps of adding a polypeptide moiety $X_n$, where n=1–3, and where a terminal amino acid is selected from the group consisting of Pro, Met and Arg, to one end of the polypeptide drug substance, and adding a protecting moiety to the opposite end of the polypeptide drug substance.

Alternatively, the invention of the instant application provides a method to enhance the absorption and bioavailability of an active polypeptide drug substance of the form $aa_n$ in a pharmaceutical formulation, the method comprising the step of formulating the active polypeptide drug substance with a terminal amino acid selected from the group consisting of Pro, Met and Arg, and with a protective moiety on the opposite terminus of the polypeptide substance, wherein the terminal amino acid (Pro, Met or Arg) is not blocked by the protective moiety.

DETAILED DESCRIPTION OF THE INVENTION

In one embodiment, the present invention provides a pharmaceutical composition for use in the treatment of physiological conditions comprising a carrier moiety and a therapeutically active peptide species as defined above. The carrier comprises an aryl or alkyl group of sufficient length and/or steric bulk to inhibit rapid enzymatic degradation of the active drug species in viva. A preferred carrier is selected from a group comprising cinnamoyl, benzoyl, phenylacetyl, 3,4-methylenedioxycinnamoyl, 3,4,5-trimethoxycinnamoyl, t-butoxycarbonyl, benzyloxycarbonyl, pivaloyl, N-9-fluorenylmethoxycarbonyl, and Fumaroyl. The carrier moiety is chemically linked to a therapeutic polypeptide of the general formula $aa_n$, where aa is an amino acid, or a chemical or structural variation thereof as defined above, where n is an integer from 2 to 40, and wherein the polypeptide is poorly absorbed orally. Preferably, in the drug composition of the invention, n is an integer from 3 to 6. More preferably, n is 5. In a particularly preferred embodiment, the polypeptide is Tyr-Gly-Gly-Phe-Met (SEQ ID NO: 1)[1]

[1] Tyr=Tyrosine; Gly=Glycine; Phe=Phenylalanine; Met=Methionine.

In an alternative variation, the pro-drug of the present invention further comprises a linker species linking the peptide to the carrier species. Preferably, the linker species is a natural peptide, a pseudo-peptide, a peptide mimic of less than 4 residues, either directly bound to the carrier or through a —$C_6$ or —$C_8$ acidic moiety, or a composition thereof. A preferred linker is the pseudo-peptide Gly-carba-Gly associated, or not, to a —$C_6$ or a —$C_8$ chain. Thus, the present invention can be viewed as a three-component entity: The first, therapeutically active component is the peptide; the second is the linker species, and the third is the carrier moiety.

When delivered orally, the drug composition of the present invention is capable of delivery a systemic dose of the active drug species to a patient ingesting the pro-drug. The active peptide, normally immediately degraded in the gastrointestinal tract to non-therapeutic forms, survives due to the protective effect of the carrier component, and persists in the patient's system for prolonged periods of time. Over time, the multi-component system is slowly broken down, probably by enzymatic hydrolysis in the liver or the plasma, releasing the pharmacologically active component. An added benefit of the present invention is that the kinetics of such breakdown to release the active component are significantly slower than for the processes associated with metabolic breakdown of the unmodified polypeptide drug species, effectively permitting a sustained, controlled release of the active species into the patient's system, thus maintaining pharmacologically effective blood serum levels over an extended period of time.

In another embodiment, the present invention contemplates a pharmaceutical composition comprising a similar multi-component entity which, when administered through a parenteral route, makes use of protective activity towards the enzymatic breakdown provided by association of the active drug species with the carrier and/or linking components, increasing thereby the in vivo half-life of the therapeutic component and improving its pharmacological properties. A preferred therapeutic moiety for use in this embodiment of the present invention is an epitope or an immune sequence characteristic of an infectious, viral or cancerous disease. This invention, therefore, provides a delivery method for such immune competent peptides that enhances their pharmacological efficacy.

In yet another embodiment, the present invention contemplates a pharmaceutical composition as defined above comprising a carrier moiety comprising an aryl or alkyl group, optionally a linker species, and a therapeutic polypeptide of the general formula $aa_n$, where aa is an amino acid, or a chemical or structural variation thereof, where n is an integer from 2 to 40, and a pharmaceutically effective adjuvant species.

As would be recognized by one of skill in the appropriate art area, one or more of the amino acids of the therapeutically active polypeptides used in conjunction with the present invention may be modified chemically or conformationally without significantly diminishing, or preferably enhancing, the pharmacological activity of the therapeutic entity. These modified polypeptides may be used in the practice of the present invention.

Ideally, the pro-drug of the present invention is formulated into a pharmaceutical composition with pharmaceutically acceptable adjuvants known to those of skill in the art of pharmaceutical formulation chemistry.

Known therapeutically active polypeptide species that have been demonstrated to be pharmacologically ineffective when delivered through typical oral routes of administration can be modified through linkage to a carrier species to achieve effective bioavailability of the active entity, as well as therapeutically effective controlled release of the active species.

In another embodiment, the invention of the instant application encompasses a method for the treatment of a physiological condition through the oral or parenteral administration of a therapeutically effective species comprising the steps of chemically linking a therapeutic polypeptide of the general formula $aa_n$, where aa is an amino acid, or a chemical or structural variation thereof, where n is an integer from 2 to 40, and wherein the polypeptide is poorly absorbed orally, to an alkyl or aryl carrier moiety preferably selected from the group comprising cinnamoyl, benzoyl, phenylacetyl, 3,4-methylenedioxycinnamoyl, 3,4,5-trimethoxycinnamoyl, t-butoxycarbonyl, benzyloxycarbonyl, pivaloyl, N-9-fluorenylmethoxycarbonyl and fumaroyl to form a pro-drug, and orally or parenterally administering the pro-drug to a patient exhibiting the physiological condition. Alternatively, in the practice of the method of the present invention, the polypeptide is chemically linked to the carrier moiety through a linker species.

Thus, utilizing the present invention, it is possible to treat physiological conditions through oral administration of therapeutically active polypeptides that would normally have to be administered through considerably less desirable routes of administration or with less effectiveness.

The present invention provides that the absorption and bioavailability of an active polypeptide drug substance can be greatly enhanced by application of either one of the following two strategies: addition of a polypeptide moiety $X_n$ (n=1–3) ending with an amino acid selected from the group consisting of Pro, Met and Arg to one end of the active polypeptide drug substance, along with the addition of a protecting moiety to the opposite end of the active polypeptide; or, alternatively, through formulation of the active polypeptide drug substance, or pro-drug entity, with a terminal amino acid selected from the group consisting of Pro, Met and Arg, with the protective moiety on the opposite terminus of the polypeptide substance, provided that the terminal amino acid (Pro, Met or Arg) is not blocked by the protective moiety.

In still another embodiment, the invention of the instant application provides a method for the controlled release administration of a therapeutically effective polypeptide of the general formula $aa_n$, where aa is an amino acid, or a chemical or structural variation thereof, where n is an integer from 2 to 40, and wherein the polypeptide is poorly absorbed orally, comprising the steps of chemically linking the polypeptide to an aryl or alkyl carrier moiety preferably selected from the group comprising cinnamoyl, benzoyl, phenylacetyl, 3,4-methylenedioxycinnamoyl, 3,4,5-trimethoxycinnamoyl, t-butoxycarbonyl, benzyloxycarbonyl, pivaloyl, N-9-fluorenylmethoxycarbonyl and fumaroyl to form a pro-drug, and orally administering the pro-drug to a patient. In a preferred embodiment, the polypeptide is chemically linked to the carrier moiety through a linker species, and, more preferably still, the linker species is an amino acid, a pseudo-peptide or a peptide mimic optionally bound to the carrier through a —$C_6$ or —$C_8$ acidic residue. Due to the kinetics of the presumed enzymatic degradation of the pro-drug of the present invention, the therapeutically active polypeptide species is released to the patient's system over relatively long periods of time, in a dosage-dependent manner, for up to twenty-four hours.

EXAMPLES

Met-Enkephalin (Tyr-Gly-Gly-Phe-Met) (SEQ ID NO: 1) is a naturally occurring pentapeptide (n=5) belonging to the endorphin class. It is known to be involved in the basic mechanisms of analgesia. It produces a transient analgesic effect when administered parenterally, but no effect has been observed when given orally. Its mechanism of action is believed to involve binding to opioid delta receptors in the brain. Met-Enkephalin is very rapidly degraded in viva into a tetra-peptide that is subsequently metabolized. As for the pharmacokinetics of Met-Enkephalin, the plasma levels of the pro-drug, as well of those of the metabolites, are barely measurable, even when administered parenterally.

Example 1

Analgesic Effects from Administration of CY5M, a Cinnamoyl-Met-Enkephalin Pro-Drug of the Present Invention According to the present invention, a pro-drug, designated CY5M for convenience of reference, comprising cinnamoyl-Met-Enkephalin (cinnamoyl-Tyr-Gly-Gly-Phe-Met), of the general form carrier-$aa_5$, demonstrated an unexpectedly strong, long-lasting analgesia in a hot plate test with rats both when administered orally, and when administered parenterally.

Methods and Materials

Analgesic activities are classically demonstrated in a hot plate test using rats as test animals. The time to first licking of the posterior foot by the rat is recorded after the rat has been place on a hot plate maintained at an elevated temperature (40° C.). This procedure provides accurate data on central analgesic activities induced by various candidate drugs. Under placebo conditions, the time to first licking of the posterior foot of the test animal varies between 30 and 50 seconds. A strong analgesia is demonstrated when this time is more than doubled. In the experiments reported herein, a standard hot plate test was used to assess analgesia and the time to first licking of the test animal's posterior foot was used as the triggering event for measurement of elapsed time as indicative of the pharmacological effect of the administered drug species.

Seven groups of five male Wistar rats each were randomly assigned to the following treatments: placebo, 1 mg/kg morphine (i.v.), 10 mg/kg morphine (oral), 10 mg/kg codeine (oral), 10 mg/kg ibuprofen (oral), 2.5 mg/kg CY5M (i.v.), and 2.5 mg/kg CY5M (oral). The method was pre-validated with two oral and i.v. administrations of saline placebo and the results were similar to those obtained with placebo in the experiment reported below.

i.v., is at least 8 times more effective than morphine by the same route of administration. Of further interest, the above data also indicate that in no case did morphine exhibit an analgesic effect lasting longer than six hours, whereas both oral and i.v. administrations of CY5M demonstrated a significant analgesic effect for a period of time of 24 hours or longer.

It is also anticipated that an analog of CY5M comprising a linker species in addition to the cinnamoyl carrier species, will demonstrate similar or greater effects than those provided above.

These results indicate that using a carrier such as disclosed herein in association with a polypeptide drug species, permits the effective oral absorption of peptides of at least 5 amino acids in length and allows a much stronger pharmacological effect, with significantly enhanced pharmacokinetic profiles, by both oral and i.v. routes of administration.

SEQUENCE LISTING

<160> NUMBER OF SEQ ID NOS: 1

<210> SEQ ID NO 1
<211> LENGTH: 5
<212> TYPE: PRT
<213> ORGANISM: Homo sapiens

<400> SEQUENCE: 1

Tyr Gly Gly Phe Met
1               5

Results

TABLE 1

Time to first signal activity after oral administration

| Time | 0 h | 1 h | 2 h | 4 h | 6 h | 24 h |
|---|---|---|---|---|---|---|
| Placebo | 53.2 | 30.6 | 38.4 | 45.0 | 46.6 | 42.0 |
| Morphine | 51.8 | 84.8 | 81.2 | 58.8 | 48.8 | 42.0 |
| Codeine | 53.2 | 51.4 | 64.6 | 57.6 | 56.2 | 46.4 |
| Ibuprofen | 53.2 | 55.0 | 70.4 | 66.0 | 54.0 | 44.2 |
| CY5M | 53.6 | 46.2 | 78.8 | 78.2 | 82.6 | 98.8 |

TABLE 2

Time to first signal activity after i.v. administration

| Time | 0 h | 1 h | 2 h | 4 h | 6 h | 24 h |
|---|---|---|---|---|---|---|
| Placebo | 53.2 | 30.6 | 38.4 | 45.0 | 46.6 | 42.0 |
| morphine | 51.8 | 118.8 | 86.6 | 63.2 | 45.6 | 40.0 |
| CY5M | 51.0 | 57.0 | 114.0 | 88.2 | 106.0 | 86.6 |

In a preliminary study (data not shown), Met-Enkephalin alone was unable to demonstrate any effect after oral administration at a 5 mg/kg dose, whereas a transient effect of about 15 minutes was observed after i.v. administration.

If one considers the area under the dose response curve a rough estimate of the average effect, the results indicate that 1 mg/kg morphine i.v. is comparable to 10 mg/kg morphine oral. In comparison, CY5M, administered either orally or by

What is claimed is:

1. A pharmaceutical agent comprising a carrier moiety and a therapeutically active peptide species, wherein the peptide has the formula $aa_n$, where n is the number of amino acid residues in the peptide and wherein the carrier is a member selected from the group consisting of cinnamoyl, benzoyl, phenylacetyl, 3,4-methylenedioxycinnamoyl, 3,4,5-trimethoxycinnamoyl, t-butoxycarbonyl, benzyloxycarbonyl, pivaloyl, N-9-fluorenylmethoxycarbonyl, and fumaroyl.

2. The pharmaceutical agent of claim 1, wherein the carrier moiety comprises an aryl or alkyl group of sufficient length or steric bulk to protect the active peptide species from enzymatic degradation in vivo.

3. The pharmaceutical agent of claim 1, wherein the carrier moiety is chemically linked to a therapeutically active peptide species of the general formula $aa_n$, where n is an integer from 2 to 40.

4. The pharmaceutical agent of claim 3, wherein the polypeptide is poorly absorbed orally.

5. The pharmaceutical agent of claim 3, wherein n is an integer from 3 to 6.

6. The pharmaceutical agent of claim 5, wherein n is 5.

7. The pharmaceutical agent of claim 3, wherein the therapeutically active peptide species comprises Tyr-Gly-Gly-Phe-Met.

8. A pharmaceutical composition for administration to a patient in need thereof comprising the pharmaceutical agent of claim 1, and one or more pharmaceutically acceptable adjuvants.

9. The pharmaceutical composition of claim 8, wherein the composition is formulated for oral administration.

10. The pharmaceutical composition of claim 8, wherein the composition is formulated for parenteral administration.

11. The pharmaceutical composition of claim 10, wherein the composition is formulated for intravenous administration.

12. The pharmaceutical composition of claim 8, wherein the composition releases a biologically active form of the pharmaceutical agent into the patient's system at physiologically effective levels over a period of time of up to twelve hours.

13. The pharmaceutical composition of claim 8, wherein the composition releases a biologically active form of the pharmaceutical agent into the patient's system at physiologically effective levels over a period of time of up to twenty-four hours.

14. The pharmaceutical composition of claim 10, wherein the peptide species is an epitope or an immune sequence characteristic of an infectious, viral or cancerous disease.

* * * * *